United States Patent
Hunt et al.

(10) Patent No.: US 8,262,885 B2
(45) Date of Patent: Sep. 11, 2012

(54) DIELECTROPHORETIC TWEEZERS APPARATUS AND METHODS

(75) Inventors: Thomas Hunt, Portland, OR (US); Robert Westervelt, Lexington, MA (US); Ania Bleszynski, Thousand Oaks, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 875 days.

(21) Appl. No.: 12/085,193

(22) PCT Filed: Nov. 6, 2006

(86) PCT No.: PCT/US2006/043137
§ 371 (c)(1),
(2), (4) Date: Feb. 13, 2009

(87) PCT Pub. No.: WO2007/058804
PCT Pub. Date: May 24, 2007

(65) Prior Publication Data
US 2009/0219647 A1     Sep. 3, 2009

Related U.S. Application Data

(60) Provisional application No. 60/738,207, filed on Nov. 18, 2005, provisional application No. 60/763,156, filed on Jan. 27, 2006.

(51) Int. Cl.
*B01D 57/02* (2006.01)
(52) U.S. Cl. ...................................... 204/547; 204/643
(58) Field of Classification Search .................. 204/547, 204/229.5, 643
See application file for complete search history.

(56) References Cited

U.S. PATENT DOCUMENTS

| | | | |
|---|---|---|---|
| 4,956,065 | A | 9/1990 | Kaler |
| 5,589,047 | A | 12/1996 | Coster et al. |
| 5,835,477 | A | 11/1998 | Binnig |
| 5,936,237 | A | 8/1999 | van der Weide |
| 6,649,402 | B2 | 11/2003 | Van der Weide et al. |
| 6,697,010 | B1 | 2/2004 | Lam |

(Continued)

FOREIGN PATENT DOCUMENTS

DE     4231426 A1    4/1993

(Continued)

OTHER PUBLICATIONS

Deveau, Jason S.T. et al., "An improved method for constructing and selectively silanizing double-barreled, neutral liquid-carrier, ion-selective microelectrodes," Biol. Proced. Online, Apr. 18, 2005; 7(1): 31-40.

(Continued)

*Primary Examiner* — J. Christopher Ball
(74) *Attorney, Agent, or Firm* — Wolf, Greenfield & Sacks, P.C.

(57) ABSTRACT

Dielectrophoretic (DEP) tweezers apparatus and methods for various applications, including particle trapping. Two electrodes are disposed on or otherwise constitute an elongated object forming a tip. A voltage is applied across these electrodes to produce a non-uniform electromagnetic field proximate to the tip thereby creating a dielectrophoretic trap. Once trapped, a particle may be moved to desired locations via manipulation of the elongated object or the medium in which the particle is located. Multiple DEP tweezers apparatus may be arranged to form arrays of tips capable of respectively generating local electromagnetic fields confined to the tips. Such DEP arrays may be employed in nanofabrication processes involving nanolithography or nano-manipulation, as well as data storage and retrieval applications.

16 Claims, 7 Drawing Sheets

U.S. PATENT DOCUMENTS

| | | | |
|---|---|---|---|
| 6,801,029 | B2 | 10/2004 | van der Weide et al. |
| 6,845,655 | B2 | 1/2005 | van der Weide et al. |
| 2004/0254457 | A1 | 12/2004 | van der Weide |
| 2004/0259377 | A1 | 12/2004 | Tupper et al. |
| 2005/0112645 | A1 | 5/2005 | Segawa et al. |

FOREIGN PATENT DOCUMENTS

| | | |
|---|---|---|
| DE | 19500660 A1 | 6/1996 |
| EP | 1193216 A1 | 4/2002 |
| EP | 1381042 A2 | 1/2004 |
| EP | 1408327 A2 | 4/2004 |

OTHER PUBLICATIONS

FHC Inc., "Capillary Tubing—for Single Cell Recording and Microinjection," L022-D, pp. 14-15, http://www.fh-co.com010300.

Fiedler, S. et al., "Dielectrophoretic sorting of particles and cells in a microsystem," Analytical Chemistry, American Chemical Society, vol. 70, No. 9, May 1, 1998, pp. 1909-1915, XP000755524 ISSN: 0003-2700.

Hunt, T.P. et al., "Dielectrophoresis tweezers for single cell manipulation," May 19, 2006, Biomedical Microdevices, Kluwer Academia Publishers, B), pp. 227-230, XP019392061 ISSN: 1572-8791.

Kation Scientific, "Micropipettes & electrodes, combination electrodes in icroiontophoresis," 5 pages, printed Jul. 22, 2005, http/://members.aol.com/kations/iontophoresis/carbonelectrode.html.

Land, B. et al., "Tools for physiology labs: an inexpensive high-performance amplifier and electrode for extracellular recording," J. of Neuroscience Methods 106 (2001) 47-55.

Millar, J., "Extracellular single and multiple unit recording with carbon fibre microelectrodes," 1996, 6 pages, http://www.qmw.ac.uk/~physiol/makingCFE.html.

Seeber, D.A. et al., "Triaxial magnetic field gradient system for microcoil magnetic resonance imaging," Review of Scientific Instruments, vol. 71, No. 11, Nov. 2000, pp. 4263-4272.

Wang, X. et al., "Automated electrophysiology: high throughput of art," ASSAY and Drug Development Technologies, vol. 1, No. 5, 2003, © Mary Ann Liebert, Inc., 13 pages.

Ying, L. et al., "Frequency and voltage dependence of the dielectrophoretic trapping of short lengths of DNA and dCTP in a nanopipette," Biophysical J. vol. 86, February 224, p. 1018-1027.

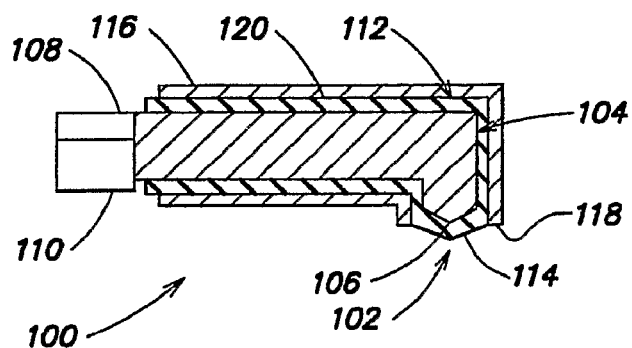
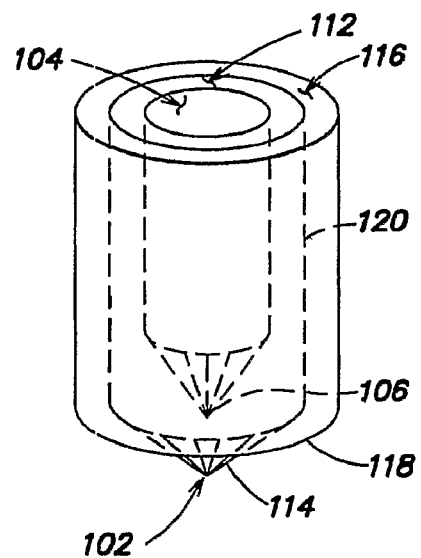
FIG. 1A
FIG. 1B
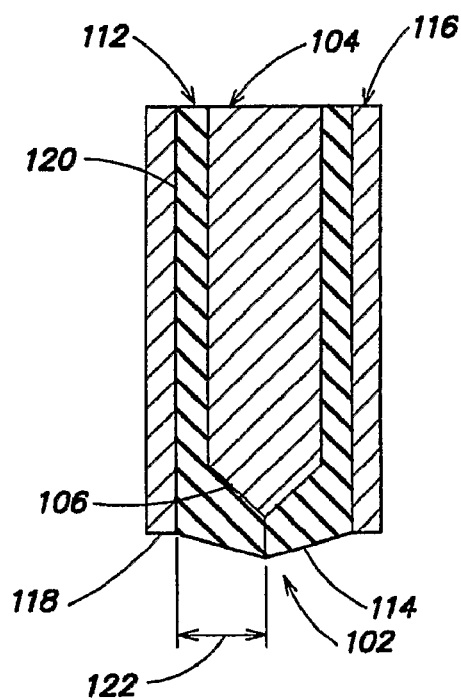
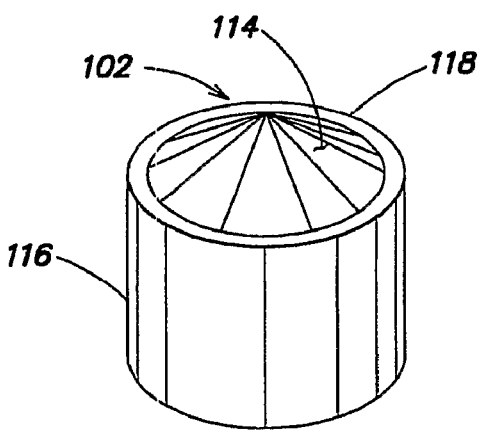
FIG. 1C
FIG. 1D

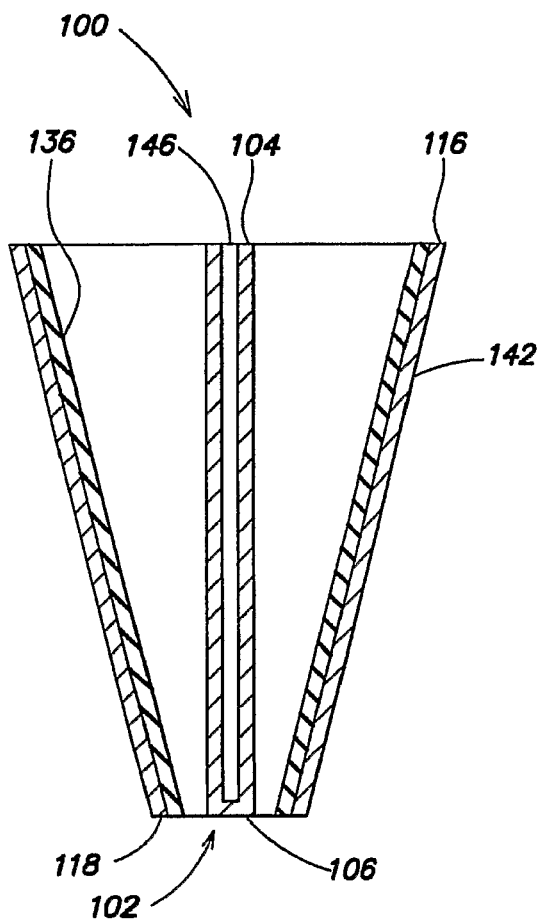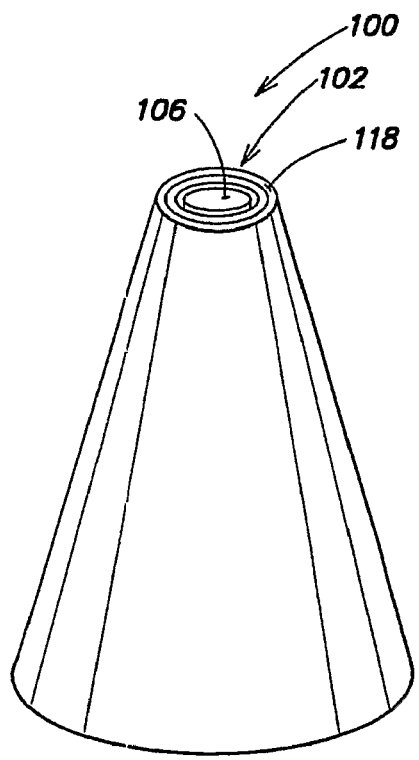
*FIG. 7A*  *FIG. 7B*
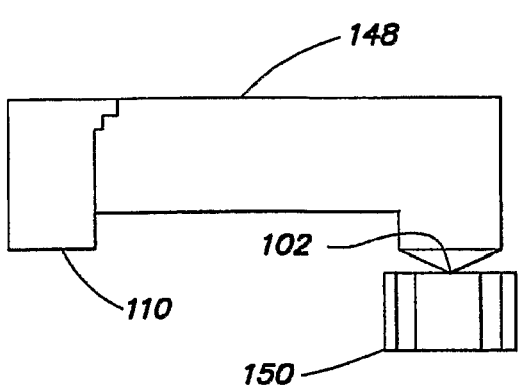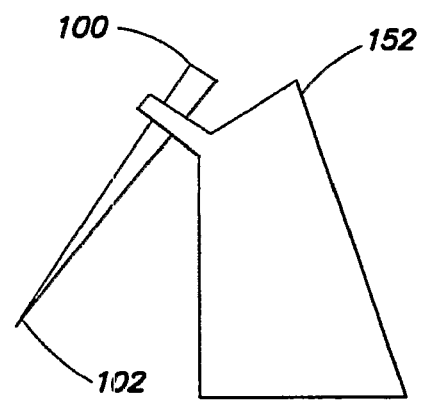
*FIG. 8A*  *FIG. 8B*

DIELECTROPHORETIC TWEEZERS APPARATUS AND METHODS

RELATED APPLICATIONS

This application is a §371 national application of International Patent Application Ser. No. PCT/US2006/043137, filed Nov. 6, 2006, which claims priority to U.S. Provisional Patent Application Ser. No. 60/738,207, filed Nov. 18, 2005, and to U.S. Provisional Patent Application Ser. No. 60/763,156, filed Jan. 27, 2006. Each of these is incorporated herein by reference.

GOVERNMENT SPONSORED RESEARCH

Various aspects of the present invention were made with U.S. Government support under the National Science Foundation, award PHY-0117795. The U.S. Government has certain rights in the invention.

BACKGROUND

It is well known that particles (e.g., atoms, molecules, cells) may have non-uniform concentrations of positive and negative charge. For instance, a molecule is made of multiple atoms that each include a positively charged center region known as a nucleus and a varying number of negatively charged subatomic particles known as electrons that exist in an outer negatively charged region around the nucleus. When the atoms combine to form the molecule, the forces associated with these two charged regions bind the atoms together. The shape of the molecule may result in a nonuniform distribution of charge, thereby producing respective concentrations of positive charge and negative charge. When this occurs, the molecule is called a polar or polarized molecule. Polarity can be induced in an otherwise non-polar molecule. Specifically, when a normally non-polar molecule is placed in a strong electromagnetic field, the negatively charged electrons are sometimes separated from the positively charged nuclei so that the otherwise non-polar molecule becomes polarized. For the purposes of the present disclosure, the terms "polar" or "polarized" are used to describe any particles that are naturally polar as well as any particles that are made polar by applying an electromagnetic field.

Since one region of a polar molecule is more positively charged and another region is more negatively charged, a force is exerted on such a molecule when it is placed into a non-uniform electromagnetic field (an electromagnetic field in which the field strength varies from one location to another). This force, known as a dielectrophoretic force, can cause the molecule to move. The exact direction of movement and velocity at which the molecule moves depends upon the particular characteristics of the molecule, the medium in which the molecule is located, and the electromagnetic field.

Specialized microscopes referred to as Scanning Probe Microscopes (SPMs) can be used to probe molecules on a scale of nanometers. One type of SPM is the Atomic Force Microscope (AFM). An AFM comprises a cantilever having a tip on one end that is scanned across a sample. Very small movements of the tip, based on variations in the profile of the surface of the sample over which the tip is scanned, are typically measured by a laser detection system and are used to generate an image of the surface profile of the scanned sample.

In some instances, the tip of an SPM need not actually make contact with the sample surface to be imaged. For example, in U.S. Pat. No. 5,936,237 to van der Weide, an SPM tip is configured as a conductor with a conducting shield around it. This configuration allows the SPM to perform a non-contact scan of a sample surface to provide an image of the surface profile based on electromagnetic field interaction between the tip and the surface. During such a scan, because no insulator separates the conducting tip from the sample, a distance is maintained between the sample and the conducting tip.

Another device commonly used with small particles is a micromanipulator. Micromanipulators are devices that move tools which are used to probe and manipulate samples on a cellular scale. Micromanipulators are used, for example, for microsurgery and other biological purposes. A micropipette is one example of a tool that can be used to probe and manipulate samples in connection with a micromanipulator. An optical microscope capable of viewing individual cells can be used to directly view a sample being manipulated by a tool coupled to a micromanipulator (hereinafter referred to as a "micromanipulator tool").

SUMMARY

The present disclosure relates generally to methods and apparatus for generating a dielectrophoretic force proximate to a tip, such as an SPM tip or micromanipulator tool tip. A tip generating such a force can then be positioned near a target particle in order to exert a force on that particle in such a way as to trap the particle (thereby creating a dielectrophoretic trap). Once a target particle is in this trap, it may be held there as long as the electromagnetic field that gives rise to the dielectrophoretic force is being generated. A tip thusly configured forms a "dielectrophoretic tweezers."

According to various embodiments of the present disclosure discussed in greater detail below, a non-uniform electromagnetic field giving rise to a dielectrophoretic force at an end of a tip is created by a pair of electrodes integrated with the tip. These electrodes can take many forms. For example, in one possible embodiment, an SPM tip itself, formed of an electrically conductive material, forms a first electrode and an insulating layer and a second electrode are placed around the tip in a coaxial configuration. An electromagnetic field providing a dielectrophoretic force proximate to the end of the tip can then be generated by applying a voltage across these first and second electrodes. The voltage can be turned on and off as desired so as to selectively trap one or more target particles.

Since an SPM tip can be moved by a user, such a tip modified in this fashion allows the user to manipulate individual trapped particles. For instance, the user can position the SPM tip near a target particle. The user can then trap the target particle by applying a voltage across the two electrodes to create the dielectrophoretic trap. Then, the user can move the trapped particle to a desired location by repositioning the SPM tip to that location. The target particle can then be released at the desired location by turning off the voltage applied to the electrodes. In other implementations, similar principles can be applied so that the tip itself is held constant while trapping the particle as a medium in which the particle is located is moved. The particle can then be released in a new region of the medium without moving the tip. Additionally, a micromanipulator can be used to control a micromanipulator tool configured with electrodes arranged to support a dielectrophoretic trap when a voltage is applied across the electrodes. This dielectrophoretic trap can be used to trap and manipulate single cells or clusters of cells.

Thus, one embodiment is directed to an apparatus comprising an elongated object forming a tip. The apparatus further comprises a first electrode that constitutes at least a first portion of the elongated object and has a first end proximate to the tip, and a second electrode that constitutes at least a second portion of the elongated object. The second electrode is insulated from the first electrode and has a second end proximate to the tip. The first end of the first electrode and the second end of the second electrode are positioned relative to each other so as to support a dielectrophoretic trap proximate to the tip.

Another embodiment is directed to a method of manipulating a particle or measuring at least one characteristic of the particle. The method comprises generating an electromagnetic field proximate to a tip formed by an elongated object, so as to support a dielectrophoretic trap proximate to the tip.

Another embodiment is directed to a method, comprising: A) generating a plurality of electromagnetic fields respectively proximate to a plurality of tips formed by a plurality of elongated objects, each elongated object comprising a first electrode having a first end proximate to a corresponding tip of the elongated object and a second electrode insulated from the first electrode and having a second end proximate to the corresponding tip; and B) positioning at least one of the plurality of tips and at least one storage medium such that the plurality of tips is proximate to the at least one storage medium so as to read information from and/or write information to the at least one storage medium based on the plurality of electromagnetic fields.

It should be appreciated that all combinations of the foregoing concepts and additional concepts discussed in greater detail below are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

FIGS. 1A-1D are four views of an AFM tip configured as a dielectrophoretic tweezers according to one embodiment of the present disclosure.

FIGS. 7A-7B are two views of a dielectrophoretic tweezers comprising a central axis according to another embodiment of the present disclosure.

FIGS. 8A-8B are views of two dielectrophoretic tweezers, each comprising a manipulator according to two implementations of the present disclosure.

DETAILED DESCRIPTION

Figure 2:
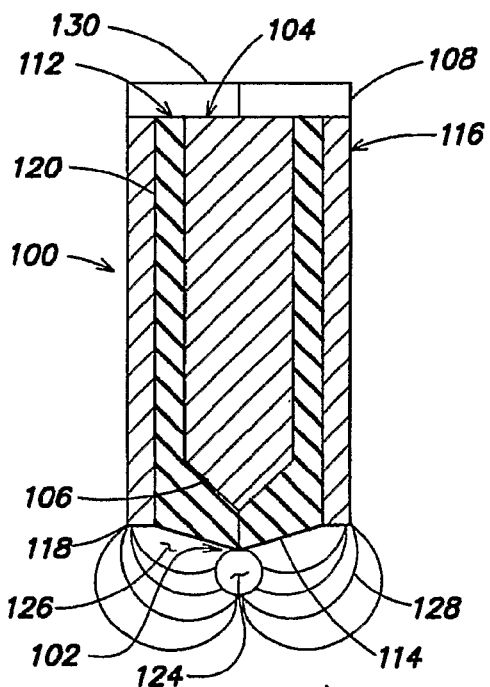
FIG. 2 is a view of the dielectrophoretic tweezers of FIGS. 1A-1D trapping a particle in a generated dielectrophoretic trap.

Following below are more detailed descriptions of various concepts related to, and embodiments of, dielectrophoretic (DEP) tweezers apparatus and methods according to the present disclosure. It should be appreciated that various concepts disclosed herein, as discussed above and outlined further below, may be implemented in any of numerous ways, as the concepts disclosed herein are not limited to any particular manner of implementation. Examples of specific implementations are provided primarily for illustrative purposes.

FIGS. 1A, 1B, 1C, and 1D illustrate four different views of a DEP tweezers apparatus based on an AFM cantilever tip configuration, according to one embodiment of the present disclosure. FIG. 1A illustrates a lengthwise cross section of the cantilever configuration of the apparatus, which forms an elongated object 100, according to this embodiment, whereas FIGS. 1B, 1C, and 1D illustrate various close-up views of a portion proximate to a tip 102 of the DEP tweezers apparatus.

The DEP tweezers apparatus shown in FIGS. 1A, 1B, 1C, and 1D has an essentially coaxial electrode configuration and comprises a first electrode 104 constituting at least a first portion of the elongated object 100. The first electrode 104 has end 106 proximate to the tip 102. One or more constituent portions of the first electrode 104 can be made from virtually any conductive material or materials. In one exemplary implementation, the first electrode 104 is formed of highly doped silicon. In one aspect, the first electrode 104 is formed of an n-type silicon having a volume resistivity of between 0.01 and 0.025 Ohm-centimeters. In another aspect, the first electrode 104 has an overall shape of an AFM cantilever and is coupled to one potential of a voltage source 108 and an AFM base 110 that provides standard AFM functionality. In yet another aspect, the end 106 of the first electrode 104 may have a radius of less than about 10 nanometers.

The DEP tweezers apparatus shown in FIGS. 1A, 1B, 1C, and 1D further comprises an electrical insulating layer 112 surrounding the first electrode 104. In particular, the insulating layer 112 includes an end portion 114 that completely surrounds the end 106 of the first electrode 104. Thus, the end portion 114 insulates the end 106 of the first electrode 104 from any sample that may be proximate to the tip 102. In particular, because of this end portion 114 of the insulating layer 112, an electrical current is essentially precluded from flowing from the first electrode 104 to a particle/sample proximate to or in contact with the tip 102.

One or more constituent portions of the insulating layer 112 can be made from virtually any insulating material. In one exemplary implementation, the insulating layer 112 is made from a single layer of silicon dioxide. Such a layer can be formed around an n-type silicon first electrode 104 by oxidizing the first electrode 104 using well known silicon-based fabrication techniques. In various other implementations, a thickness of the insulating layer 112 may vary depending on the particular use of the apparatus and the range of voltages applied across the electrodes. Generally, the thickness is sufficient to prevent breakdown of the insulating layer 112 when the desired voltage is applied. In one implementation, a thickness of the insulating layer 112 made from silicon dioxide is about 100 nanometers.

As illustrated in FIGS. 1A, 1B, 1C, and 1D, the DEP tweezers apparatus of this embodiment also comprises a second electrode 116 constituting at least a second portion of the elongated object 100. The second electrode 116 is insulated from the first electrode 104 and has an end 118 proximate to the tip 102. In one aspect, the second electrode 116 constitutes (e.g., is disposed on) at least a portion of an outer surface 120 of the insulating layer 112, such that the insulating layer 112 insulates the second electrode 116 from the first electrode 104. One or more constituent portions of the second electrode 116 can be made from virtually any conducting material or materials. In one exemplary implementation, the second electrode 116 comprises two conductive layers, namely, an inner layer of chrome and an outer layer of gold. In various aspects, the respective thicknesses of these conductive layers can vary; in one implementation, a thickness for the chrome layer is about 10 nanometers, and a thickness for the gold layer is about 30 nanometers. These conductive layers can be formed on the outer surface 120 of the insulating layer 112 by well known techniques (e.g., vapor deposition) commonly employed in silicon-based fabrication processes.

In one aspect of the embodiment illustrated in FIGS. 1A, 1B, 1C, and 1D, the end 106 of the first electrode 104 and the end 118 of the second electrode 116 are positioned relative to each other so as to support a DEP trap proximate to the tip 102. As shown in FIGS. 1B and 1D, the end 118 and the rest of the second electrode 116 are arranged in a concentric manner around the insulating layer 112. This results in a coaxial configuration where the second electrode 116 extends along the length of the first electrode 104 (as discussed above, the insulating layer 112 also extends along this length to insulate the first electrode 104 from the second electrode 116). Furthermore, in one aspect, the end portion 114 of the insulating layer 112 protrudes from the end 118 of the second electrode 116 proximate to the tip 102 and insulates the end 106 of the first electrode 104 from any sample proximate to the tip 102. If the second electrode 116 is formed on the insulating layer 112 using vapor deposition, excess conducting material near the end 118 may need to be removed to allow this end portion 114 of the insulating layer 112 to protrude from the end 118 of the second electrode 116.

As illustrated in FIG. 1C, the insulating layer 112 also forms a spacing 122 between the end 106 of the first electrode 104 and the end 118 of the second electrode 116 that is suitable for supporting a significant DEP force proximate to the tip 102. In various implementations of DEP apparatus according to the present disclosure, the spacing 122 may range between about 500 micrometers and about 5 nanometers. This spacing 122 can affect the configuration of the electromagnetic field generated when a voltage is applied across the electrodes and thereby the strength of the resulting DEP force, as described below.

In one implementation, to produce a DEP trap using the tweezers apparatus illustrated in FIGS. 1A, 1B, 1C, and 1D, a voltage source 108 is coupled to the first electrode 104 and the second electrode 116. This voltage source 108 is configured to apply a voltage between the first electrode 104 and the second electrode 116 so that an electromagnetic field is generated proximate to the tip 102. As discussed above and explained in greater detail below, a DEP trap is thereby created proximate to the tip 102 when this voltage is applied. The magnitude and frequency of the applied voltage may vary depending on the application and type of particle to be trapped. In one aspect, the voltage source 108 is configured to have at least one of an adjustable amplitude and an adjustable frequency. As discussed below, the force associated with a DEP trap can be adjusted by varying at least one of the frequency and the amplitude of the applied voltage.

The force exerted on a particle in a DEP trap depends on the Clausius-Mossotti (CM) factor, a measurement of the effective permeability of the particle relative to the medium in which the particle is located. This factor varies between a value of 1 and −0.5 and is determined by the permittivity $\in_m$ of the medium in which the particle is located, the medium conductivity $\sigma_m$, the particle permittivity $\in_p$, the particle conductivity $\sigma_p$, and the frequency of the applied electromagnetic field $\omega$. The Clausius-Mossotti factor can be determined by the following equation:

$$CM = \text{REAL}\left[\frac{(\sigma_p + \omega * \varepsilon_p) - (\sigma_m + i * \omega * \varepsilon_m)}{(\sigma_p + i * \omega * \varepsilon_p) + 2 * (\sigma_m + i * \omega * \varepsilon_m)}\right].$$

When the Clausius-Mossotti factor is positive, a force pushes the particle towards stronger areas of the electromagnetic field. When the Clausius-Mossotti factor is negative, a force pushes the particle towards weaker areas of the electromagnetic field. The force applied to a particle in an electromagnetic field having a field strength E can be determined by the following equation, where $\in_0$ is the permittivity of free space and $\alpha$ is the radius of the particle:

$$\text{Force} = 3 * \pi * \alpha^3 * \in_0 * CM * \nabla(E^2).$$

Finite element methods can be used to determine the $\nabla(E^2)$ term in this equation for a given electromagnetic field. This term varies based on the applied voltage and the configuration of the electrodes. As an example, consider a DEP tweezers apparatus as shown in FIGS. 1A, 1B, 1C and 1D having a spacing 122 of d between the end 106 of the first electrode 104 and the end 118 of the second electrode 116. A voltage with a magnitude V applied across these two electrodes generates an electromagnetic field proximate to the tip 102 with an estimated strength E=V/d. Without using finite element methods, the value of the term $\nabla(E^2)$ can be reasonably estimated as $V^2/d^3$.

To illustrate the creation of a DEP trap, consider the apparatus displayed in FIG. 2. In FIG. 2, a target particle 124 is trapped in DEP trap 126 produced by electromagnetic field 128, which is generated by applying a voltage having magnitude V across the two electrodes 104 and 116. The frequency of this voltage determines the frequency of the electromagnetic field 128. Suppose that the electromagnetic field 128 is generated having a frequency $\omega$ such that the Clausius-Mossotti factor (CM) equals 1. Suppose also that target particle 124 has a radius a equal to d/2 (where d represents the spacing 122 indicated by FIG. 1C). From the force equation given above, and using the approximation $\nabla(E^2) \approx V^2/d^3$, if the radius a of the target particle 124 is 5 micrometers and the magnitude V of the voltage applied across the electrodes 104 and 116 is 10 Volts, the force exerted on the target particle 124, which force creates the DEP trap 126, is approximately 1000 picoNewtons.

The force needed to effectively trap the target particle 124 varies depending on what other forces may be acting on the particle 124. Typically, between 10 picoNewtons and 1000 picoNewtons is sufficient to trap the particle 124. For example, a force just greater than 10 picoNewtons normally is sufficient to trap a protein, because typical forces that bind proteins together are on the order of approximately 10 picoNewtons. As forces acting on the particle 124 in the medium in which it is found increase, the DEP force needed to trap the particle 124 increases accordingly. Furthermore, external forces may act to remove the particle 124 from the DEP trap 126. For example, when the particle 124 is moved through a medium, such as by moving the DEP tweezers apparatus while the particle 124 is trapped in DEP trap 126, a drag force may act to remove the particle 124 from the trap 126. The force holding the particle 124 in the DEP trap 126 must be great enough to overcome this drag force and any other external forces that may be acting on the particle 124.

The medium in which the particle 124 is found also may play an important role in determining what frequency of voltage to apply across the first and second electrodes 104 and 116. A low frequency voltage is appropriately used to create a DEP trap 126 in a gas or vacuum. In some cases, a DC (i.e., zero-frequency) voltage is appropriate in these mediums.

However, in a fluid medium, a higher frequency voltage (e.g., from 10 kHz to greater than 1 MHz) may be more appropriate for creating the DEP trap 126. In some circumstances, a frequency into the GHz range is appropriate. A high frequency is desirable in some applications involving a fluid medium because ions in the fluid medium produce a fluid flow when a low frequency electromagnetic field is generated in the fluid. This fluid flow can disrupt the DEP trap 126. Generating a relatively higher frequency electromagnetic field helps prevent this fluid flow and leaves the DEP trap 126 effectively undisturbed.

Additionally, use of a high frequency electromagnetic field in a fluid prevents ions in the fluid from creating a shield around the DEP trap 126. At low frequencies, these ions may form a shield around the DEP trap 126, thereby blocking the DEP trap 126 from the rest of the fluid including the target particle 124. At higher frequencies, these ions are unable to move to form such a shield, and the DEP trap 126 is thereby free to trap the target particle 124.

In some implementations of the present disclosure, as illustrated in FIG. 2, the DEP tweezers apparatus may include a device 130 that can measure capacitance or conductance between the two electrodes 104 and 116. Since the capacitance and conductance vary based on a presence or an absence of the particle 124 in the DEP trap 126, the device 130 may be used to sense the presence or the absence of the particle 124 in the DEP trap 126. In one implementation of the present disclosure in which the DEP tweezers apparatus includes the voltage source 108 with an adjustable frequency or amplitude and the device 130, the frequency or amplitude of the voltage applied across the electrodes 104 and 116 may be varied while the device 130 measures the capacitance or the conductance across the electrodes. By measuring the capacitance or conductance across the electrodes over a range of frequencies or amplitudes, information about the trapped particle 124, including but not limited to information relating to the composition of the particle 124, can be determined.

The voltage source 108 of some implementations of the present disclosure may be configured to apply a current to a particle/sample 124 proximate to or in contact with the tip 102. For example, if either of the electrodes 104 or 116 of the DEP tweezers apparatus according to various embodiments discussed herein is put in contact with the particle/sample, voltage can be applied to that electrode thereby causing a current to flow to the particle/sample. In some embodiments, one of the electrodes is specifically shielded from a sample to prevent unwanted current flow (e.g., the first electrode 104 in FIGS. 1A-1D), but in those embodiments, a voltage can still be applied to the other electrode to cause a current to flow to the particle/sample. This process may be particularly useful for stimulating individual untrapped muscle or nerve cells located proximate to the tip 102 of the apparatus.

The various embodiments described above are only some of many possible embodiments for a DEP tweezers apparatus. Other possible embodiments may include tips of other types of SPMs, AFM tips, micromanipulator tool tips, sharpened glass tips, tips of other types of elongated objects, and the use of radiation with a DEP tweezers apparatus. Some of these other embodiments are discussed below.

Figure 3A:
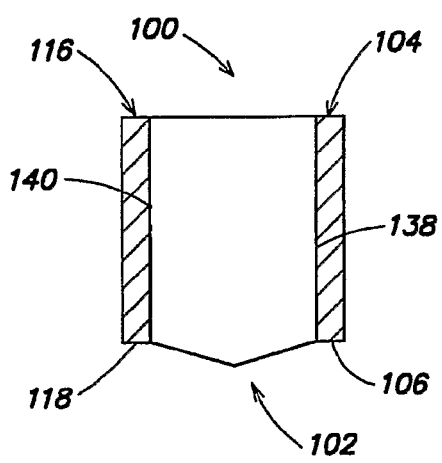
FIGS. 3A-3B are two views of a dielectrophoretic tweezers according to another embodiment of the present disclosure.
Figure 3B:
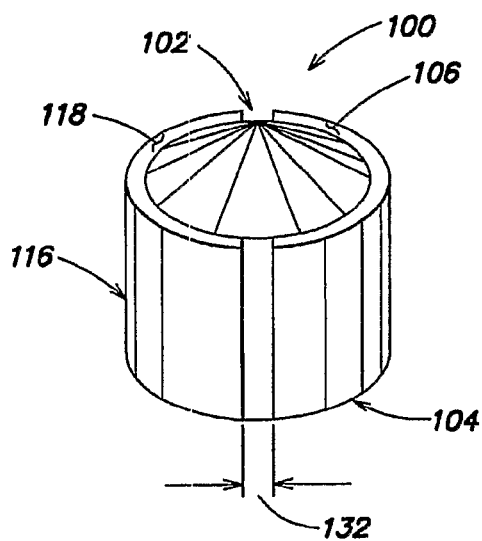

FIGS. 3A and 3B illustrate two different close-up views of the tip 102 of another embodiment of a DEP tweezers apparatus according to the present disclosure. As discussed above with respect to other embodiments, the DEP tweezers apparatus shown in FIGS. 3A and 3B comprises a first electrode 104 constituting at least the first portion of the elongated object 100. The first electrode 104 has end 106 proximate to the tip 102. This embodiment of a DEP tweezers apparatus also comprises a second electrode 116 constituting at least the second portion of the elongated object 100. The second electrode 116 has end 118 proximate to the tip 102.

Figure 4:
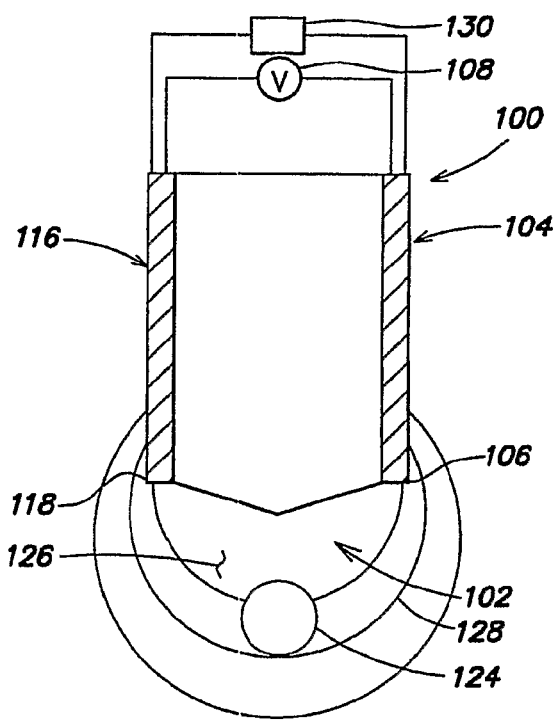
FIG. 4 is a view of a dielectrophoretic tweezers of FIGS. 3A-3B trapping a particle in a generated dielectrophoretic trap.

In the embodiment illustrated by FIGS. 3A and 3B, the first electrode 104 and the second electrode 116 constitute (e.g., are disposed on) opposing sides of the elongated object 100. An insulating gap 132 insulates the first electrode 104 from the second electrode 116. FIG. 4 illustrates the trapping of a target particle 124 via the DEP tweezers apparatus shown in FIGS. 3A and 3B, in a manner similar to that shown in FIG. 2. The dimensions of the insulating gap 132 shown in FIG. 3B depend on the desired voltage to be applied across the first and second electrodes and the desired characteristics of the electromagnetic field 128 to be generated proximate to the tip 102. Generally, the insulating gap 132 has dimensions suitable to support the DEP trap 126 proximate to the tip 102 and to prevent breakdown of the insulating gap when the desired voltage is applied across the first and second electrodes 104 and 116. In one implementation of this embodiment, the insulating gap will separate the first electrode 104 and the second electrode 116 by a distance between about 500 micrometers and about 5 nanometers.

Figure 5A:
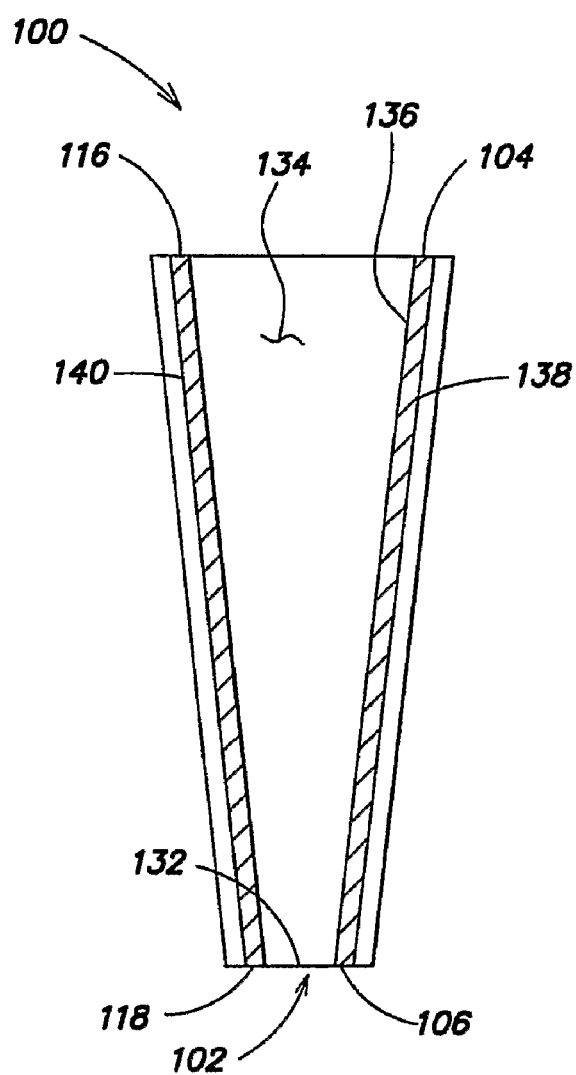
FIGS. 5A-5B are two views of a dielectrophoretic tweezers comprising a hollow elongated object according to another embodiment of the present disclosure.
Figure 5B:
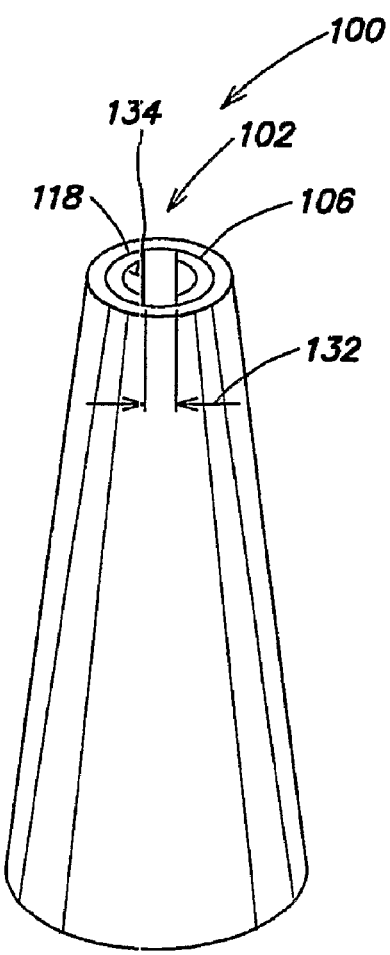

FIGS. 5A and 5B illustrate two different close-up views of the tip 102 of another embodiment of a DEP tweezers apparatus according to the present disclosure. DEP tweezers apparatus configured according to this embodiment may be particularly useful as micromanipulator tools, including micropipettes.

The elongated object 100 illustrated in FIGS. 5A and 5B has a hollow core 134 that creates an interior surface 136 of the elongated object 100. The first electrode 104 constitutes the first portion of the elongated object 100 that, in this embodiment, corresponds to a first side 138 of the interior surface 136 of the elongated object 100. As in other embodiments discussed above, first electrode 104 has end 106 proximate to the tip 102. In the illustrated embodiment of FIGS. 5A and 5B, second electrode 116 constitutes at least a second portion of the elongated object 100 that, in this embodiment, corresponds to a second side 140 of the interior surface 136 of the elongated object 100. As in other embodiments discussed above, second electrode 116 has end 118 proximate to the tip 102.

In one implementation of this embodiment, the second electrode 116 is insulated from the first electrode 104 because the first electrode 104 and second electrode 116 are disposed on opposing sides 138 and 140 of the interior surface 136 of the elongated object 100 and are separated by at least a portion of hollow core 134. In one aspect of such an implementation, illustrated by FIGS. 5A and 5B, the insulating gap 132 ensures that the first electrode 104 and second electrode 116 are insulated from each other at the point where the first side 138 and second side 140 are closest to each other. The dimensions of the insulating gap 132 and the hollow core 134, in general, depend on the desired voltage to be applied across the electrodes and the desired characteristics of the electromagnetic field 128 generated proximate to the tip 102 (e.g., as discussed above in connection with FIG. 2). Generally, the insulating gap 132 and the hollow core 134 have dimensions suitable to support the DEP trap 126 proximate to the tip 102 and to prevent breakdown of the insulating gap 132 and the hollow core 134 when the desired voltage is applied across the first and second electrodes 104 and 116. In one implementation of such an embodiment, the insulating gap separates the first electrode 104 and the second electrode 116 by a distance between about 500 micrometers and about 5 nanometers.

Figure 6A:
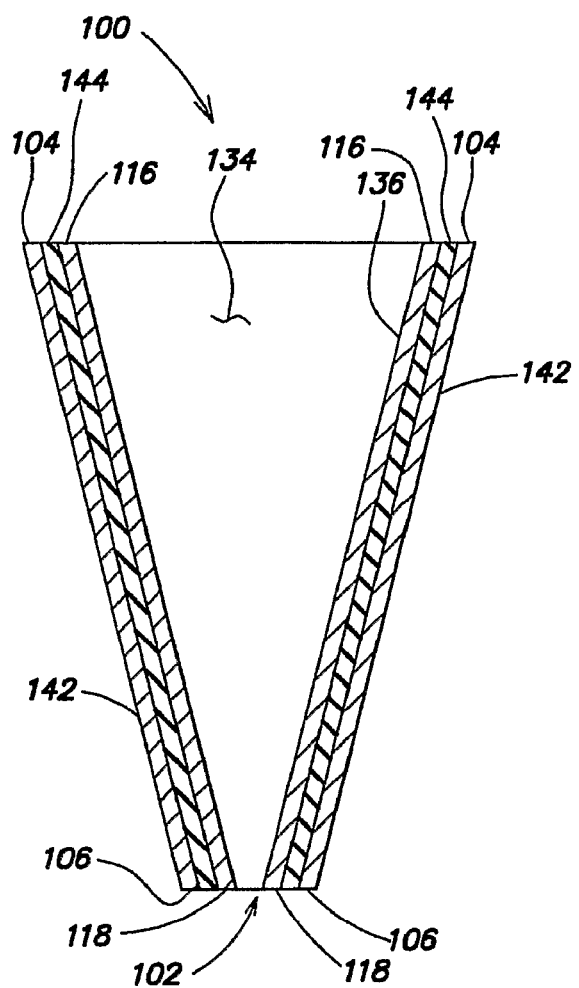
FIGS. 6A-6B are two views of a dielectrophoretic tweezers comprising a hollow elongated object according to another embodiment of the present disclosure.
Figure 6B:
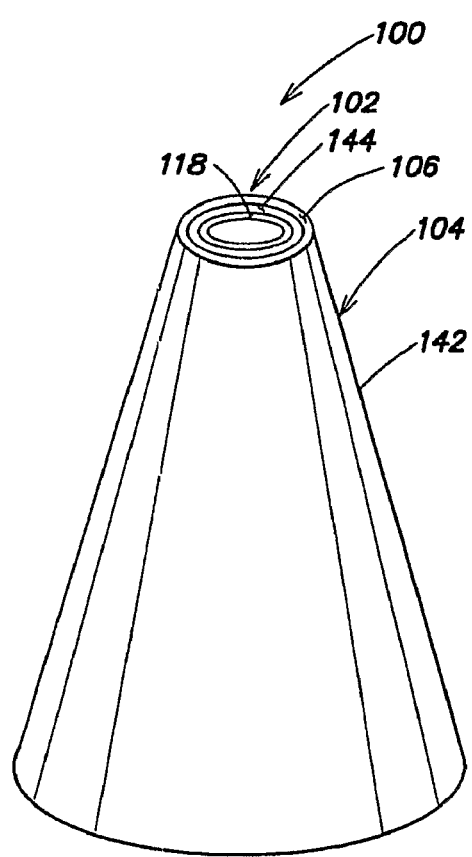

Another embodiment of a DEP tweezers apparatus according to the present disclosure is illustrated in FIGS. 6A and 6B. In this embodiment, hollow core 134 forms the interior surface 136 of the elongated object 100. First electrode 104 constitutes the first portion of elongated object 100 that, in this embodiment, corresponds to at least a portion of an outer perimeter surface 142 of the elongated object 100. The first electrode 104 has end 106 proximate to tip 102. Second electrode 116 constitutes at least the second portion of the elongated object 100 that, in this embodiment, corresponds to at least a portion of the interior surface 136 of the elongated object 100. The second electrode 116 has end 118 proximate to the tip 102.

In one implementation of this embodiment, an insulating wall 144 of the elongated object 100 insulates the first electrode 104 from the second electrode 116. In one aspect of this implementation, as illustrated in FIGS. 6A and 6B, the first electrode 104 and second electrode 116 are arranged in a concentric manner. Generally, the insulating wall 144 has dimensions suitable to support the DEP trap 126 proximate to the tip 102 and to prevent breakdown when a desired voltage is applied across the first and second electrodes 104 and 116.

Still another embodiment of the present disclosure is illustrated in FIGS. 7A and 7B. In this embodiment, the elongated object 100 comprises a central axis 146 that passes though the elongated object 100. First electrode 104 constitutes the portion of the elongated object 100 that, in this embodiment, corresponds to at least a part of the central axis 146. Second electrode 116, in one implementation of this embodiment, constitutes the portion of the elongated object 100 that corresponds to the outer perimeter surface 142 of the elongated object 100. In another implementation, the second electrode 116 constitutes the portion of the elongated object 100 that corresponds to the interior surface 136. In one aspect of this embodiment, the resulting configuration may be such that the first electrode 104 and the second electrode 116 are essentially concentric and insulated from each other. The arrangement of the electrodes may vary but generally supports the DEP trap 126 proximate to the tip 102 and prevents breakdown when a desired voltage is applied across the first and second electrodes 104 and 116.

Any DEP tweezers apparatus embodiment may include at least one manipulator coupled to the tip 102, as illustrated in FIGS. 8A and 8B. In some implementations, the manipulator may be configured to move the tip 102 from one location to another location. As described above, if the tip 102 is moved from one location to another while the particle 124 is trapped in the DEP trap 126, the particle 124 will move with the tip 102. In some other implementations, the manipulator may be configured to hold the tip 102 in place and move the medium in which the particle 124 is located. As described above, if the medium is moved while the particle 124 is trapped, the particle 124 can be released in a new region of the medium. The manipulator may comprise any type of device capable of moving either the tip 102 or the medium, including, as illustrated in FIG. 8A, a SPM 148 and a piezotube 150, and, as illustrated in FIG. 8B, a micromanipulator 152.

As illustrated in FIGS. 9A, 9B, 9C and 9D, some embodiments of a DEP tweezers apparatus according to the present disclosure may be configured to allow radiation 154 to pass to or from a particle 124 trapped proximate to the tip 102. In one aspect of this embodiment, the interaction of radiation with a trapped particle, and the capability to direct radiation to or from the trapped particle via the DEP tweezers apparatus, may facilitate another methodology for particle characterization based on a particle's sensitivity and response to various wavelengths of radiation. To this end, the transported radiation 154 may comprise virtually any wavelength, including visible light, and may have a variety of bandwidths (e.g., from narrowband/monochromatic to substantially broader band spectra).

In various implementations, a given DEP tweezers apparatus itself may be configured to direct first radiation to a trapped particle, and also direct second radiation reflected or emitted from the particle in response to the first radiation. Alternatively, a particle may be irradiated from a source not necessarily associated with the DEP tweezers apparatus, but radiation reflected by or emitted from the irradiated particle may be directed by the DEP tweezers apparatus (e.g., to some measurement or sensing device). Similarly, the DEP tweezers apparatus may be configured merely to direct radiation to impinge upon a trapped particle, and any other radiation emanated by the particle may be directed and/or measured by another means not necessarily associated with the DEP tweezers.

In one exemplary embodiment, the elongated object forming the DEP tweezers apparatus may be particularly configured so as to guide radiation. For instance, the elongated object may be configured so as to pass the radiation via at least one insulating medium between the first electrode and the second electrode. More specifically, one or more insulating media may be arranged so as to form a waveguide within the elongated object. In another embodiment, the elongated object may be hollow, and pass radiation via a hollow core. Alternatively, in yet another embodiment, the elongated object may include a fiber optic to guide the radiation.

Figure 9A:
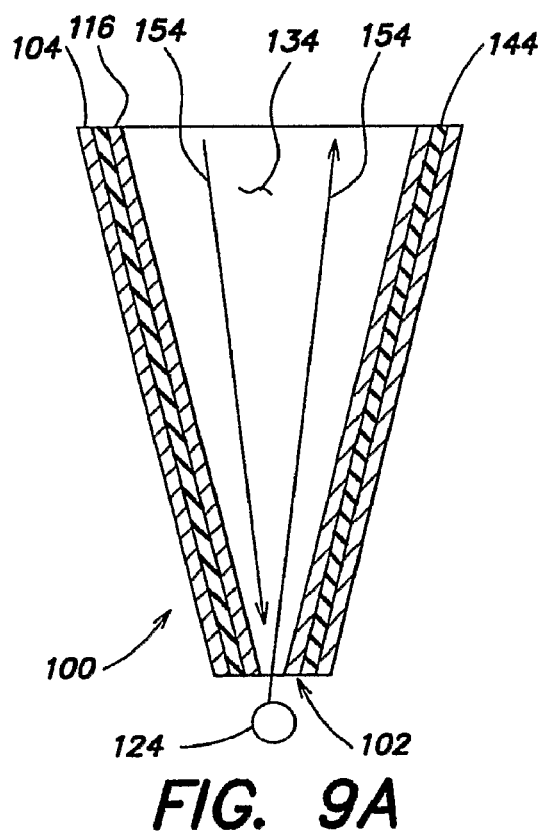
FIGS. 9A-9D are views of four dielectrophoretic tweezers configured to allow the passage of radiation according to four other implementations of the present disclosure.
Figure 9B:
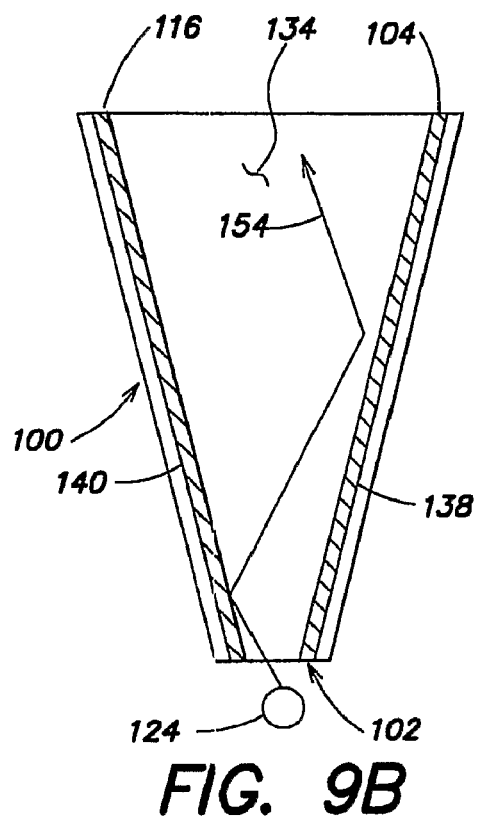
Figure 9C:
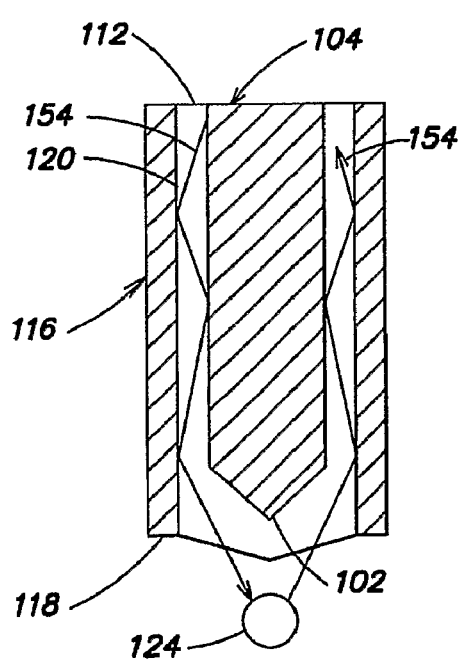
Figure 9D:
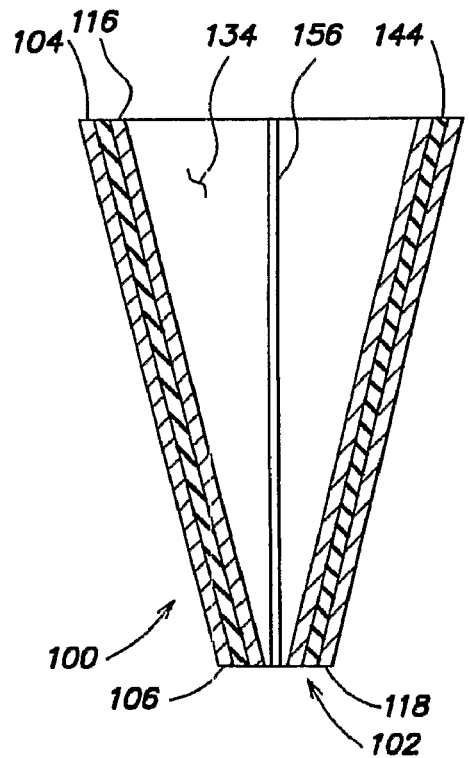

More specifically, in one exemplary implementation illustrated in FIG. 9A, radiation 154 passes through hollow core 134 of elongated object 100 to and from the trapped particle 124. In another implementation, as illustrated in FIG. 9B, the elongated object 100 is configured to guide the radiation 154. In some implementations, as illustrated in FIG. 9C, the insulating layer 112 between the first electrode 104 and second electrode 116 may be configured to guide radiation 154 to and from the particle 124. In still other implementations, the elongated object 100 may include a fiber optic 156 to guide the radiation 154, as illustrated in FIG. 9D.

With respect to applications for DEP tweezers apparatus, in one exemplary application DEP tweezers apparatus according to various embodiments of the present disclosure discussed above may be configured to perform various biological application, such as electroporation of a cell proximate to the tip 102. The voltage source 108 of such implementations is configured to apply a properly timed pulse so that the electromagnetic field 128 generated thereby proximate to the tip 102 temporarily increases permeability of a cell membrane of the cell. Timing of the pulse is important, as is known in the art, since an overexposure to the electromagnetic field can cause serious cell damage. Generally, the pulse has a duration of between about 10 nanoseconds and about 10 milliseconds. While the cell membrane is in an increased state of permeability, it can be exposed to a desired substance (e.g., drugs, DNA, various reagents may be injected into the cell). The increased permeability allows the desired substance to pass through the cell membrane into the cell itself without the need to physically puncture the cell membrane. The desired substance can be delivered to the cell by the DEP tweezers apparatus itself if the elongated object 100 is configured as a micropipette or similar device (e.g., as discussed above in connection with FIGS. 5A, 5B, 6A and 6B). Other biological applications based on related concepts may include in vitro fertilization and tissue assembly.

In yet another embodiment of the disclosure, multiple DEP tweezers apparatus according to any of the embodiments discussed above may be employed together in a variety of geometric configurations or arrangements. Exemplary implementations of multiple DEP tweezers apparatus may include, but are not limited to, one or two dimensional arrays forming a spatial arrangement of tips, in which controllable local electromagnetic fields respectively may be generated proximate to the ends of the tips (i.e., generally confined to a small area proximate to each tip). In various aspects of such embodiments, hereinafter referred to generally as a "DEP tweezers array" or "DEP array," each individual tweezers apparatus of the array may be operated individually and independently (e.g., via a voltage source 108, as discussed above in connection with FIGS. 2 and 4) to generate a controllable electromagnetic field, or groups of two or more tweezers apparatus may be operated together and simultaneously. Moreover, individual tweezers apparatus and/or groups of tweezers apparatus in the array may be operated in a series fashion and/or parallel fashion, so as to generate a variety of static or dynamic localized electromagnetic field patterns over an area generally encompassed by the array. In exemplary implementations, one or more voltage sources for individual or grouped members of a DEP tweezers array may in turn be controlled by a processor, computer, or other control circuitry to provide simultaneous or multiplexed variable amplitude/variable frequency voltage(s) to facilitate operation of the array.

Figure 10A:
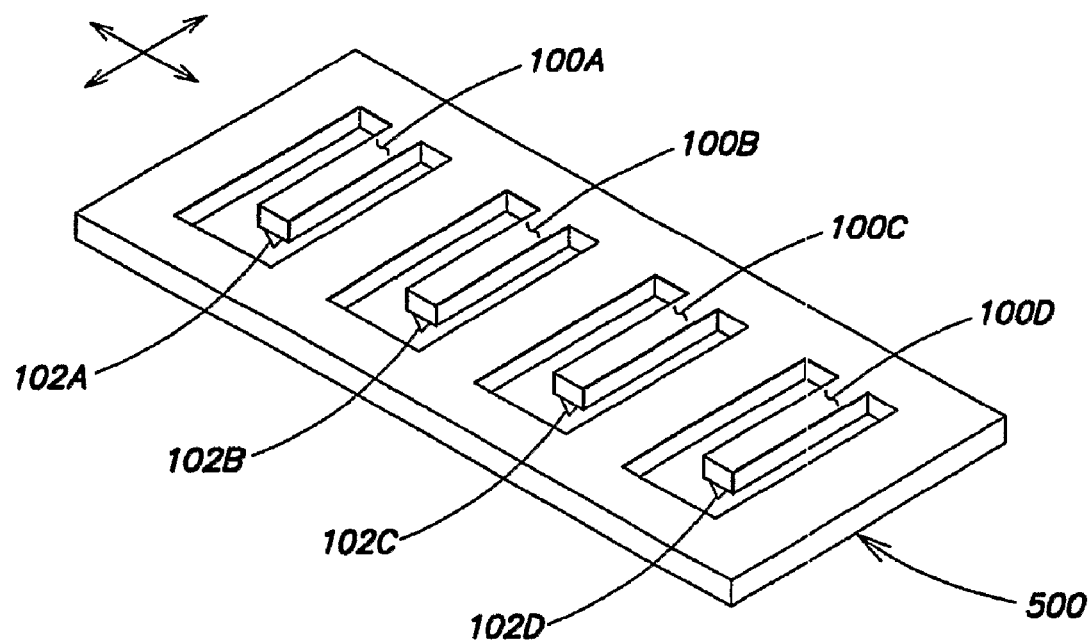
FIGS. 10A and 10B illustrate perspective and cut-away front views, respectively, of a DEP tweezers array 500 according to one embodiment of the present disclosure.
Figure 10B:
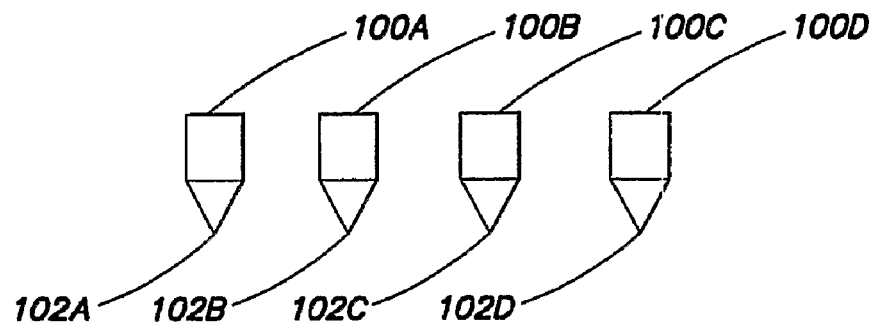

FIGS. 10A and 10B illustrate perspective and cut-away front views, respectively, of a DEP array 500 according to one embodiment of the present disclosure. The exemplary DEP array 500 includes four DEP tweezers apparatus having a cantilever configuration constituted by elongated objects 100A, 100B, 100C, and 100D with respective tips 102A, 102B, 102C and 102D. It should be appreciated that a linear arrangement of four apparatus having a cantilever configuration is shown in FIGS. 10A and 10B primarily for purposes of illustrating one exemplary array 500, and that the disclosure is not limited in this respect, as arrays according to other implementations may have different numbers, arrangements, and configurations of DEP tweezers apparatus. In one exemplary implementation, DEP tweezers apparatus having a coaxial configuration as shown in FIGS. 1A-1D may be used in the array 500, whereas in other implementations, DEP tweezers apparatus having the configuration shown in FIGS. 3A and 3B, or configurations discussed in connection with other figures, may be employed in the array 500.

In one exemplary application, DEP tweezers apparatus or a DEP array according to the present disclosure may be employed to facilitate nanofabrication processes including nanolithography and nano-manipulation (manipulation of nano-scale particles). The positioning of chemically synthesized nanoscale particles (nanowires, nanotubes, and nanocrystals) may be effectively controlled. Due to the small size of these particles, they are conventionally difficult to assemble into operational devices and circuits, particularly on the individual particle level. Nano-manipulation is a key enabling technology facilitated by the DEP trapping concepts disclosed herein for the assembly of nanoscale particle devices from single devices to circuits, and eventually to wafer-level manufacturing.

The dielectrophoretic trapping techniques disclosed herein also may be employed to separate metallic nanotubes from semiconductor nanotubes based on the difference in their electrical conductance. Using the localized electric field at the tip of a DEP tweezers apparatus, this separation can be done on a single nanotube basis. Accordingly, via the DEP tweezers apparatus disclosed herein, individual particles can be identified and separated based on their dielectric properties. As discussed above in connection with FIGS. 2 and 4 with respect to particle characterization, a frequency of the RF field that forms the DEP trap may be varied (e.g., a frequency of the voltage applied to the electrodes may be varied), and frequency-dependent parameters of the trapped particle may be measured (e.g., a frequency-dependent capacitance or conductance) to determine a spectral response that may represent one or more particular characteristics of the trapped particle (e.g., metallic vs. semiconductor).

In yet another exemplary application, the fields produced by a DEP array need not necessarily be used to trap particles, but alternatively may be used to facilitate data storage and retrieval. As discussed above, each DEP tweezers apparatus of an array can be configured and operated to produce a highly localized field that is confined to a small area proximate to the tip of the apparatus, and a collection of such fields may be used to read information from and/or write information to one or more storage media (e.g., read and write flash memory or ferroelectric bits). In general, the field confinement provided by the various DEP tweezers apparatus disclosed herein provides for a significantly smaller bit size than that achieved using conventional techniques (examples of mass-storage applications using conventional probe arrays and not employing DEP techniques are disclosed in U.S. Pat. No. 5,835,477, issued on Nov. 10, 1998 to Binnig et al., and entitled "Mass-Storage Applications of Local Prove Arrays," which patent is hereby incorporated herein by reference).

Accordingly, the concepts disclosed herein relating to dielectrophoretic forces and DEP tweezers apparatus and arrays may be employed to realize significant improvements over conventional data storage and/or retrieval techniques such as those disclosed in the above-referenced patent. For example, in one method according to the present disclosure, a DEP array (specifically, the tips of such an array) is placed proximate to one or more storage media. One or more of the DEP tweezers apparatus constituting the array are then energized so as to generate one or more electromagnetic fields proximate to one or more tips of the array, and information is read from and/or written to the storage medium/media via the one or more electromagnetic fields thusly generated. In yet another exemplary application based on a similar approach employing multiple controllable localized fields, one or more electromagnetic fields thusly generated may be employed for exposing photoresist for subsequent development.

Having thus described several illustrative embodiments, various alterations, modifications, and improvements will readily occur to those skilled in the art. Such alterations, modifications, and improvements are intended to be within the spirit and scope of the disclosure. While some examples presented herein involve specific combinations of functions or structural elements, it should be understood that those functions and elements may be combined in other ways according to the present disclosure to accomplish the same or different objectives. In particular, acts, elements and features discussed in connection with one embodiment are not intended to be excluded from similar or other roles in other embodiments. Accordingly, the foregoing description is by way of example only, and is not intended as limiting.

What is claimed is:

1. A method of manipulating and/or measuring at least one characteristic of a particle, comprising:
   A) generating an electromagnetic field proximate to a tip formed by an elongated object, so as to support a dielectrophoretic trap proximate to the tip; and
   B) moving the elongated object to at least one desired location while an electromagnetic field is generated proximate to the tip formed by the elongated object.

2. The method of claim 1, wherein a first electrode constitutes at least a first portion of the elongated object, a second electrode constitutes at least a second portion of the elongated object, the first electrode is insulated from the second electrode, and wherein the method further comprises:
   measuring a capacitance or conductance between the first electrode and the second electrode so as to sense a presence or an absence of a particle trapped in the dielectrophoretic trap.

3. The method of claim 1, wherein a first electrode constitutes at least a first portion of the elongated object, a second electrode constitutes at least a second portion of the elongated object, the first electrode is insulated from the second electrode, and wherein the method further comprises:
   measuring a capacitance or conductance between the first electrode and the second electrode so as to determine at least one characteristic of a particle trapped in the dielectrophoretic trap.

4. The method of claim 3, wherein measuring a capacitance or conductance includes measuring the capacitance or conductance at at least two different frequencies of the electromagnetic field so as to determine the at least one characteristic of the particle trapped in the dielectrophoretic trap.

5. The method of claim 1 further comprising passing radiation via the elongated object to or from a particle trapped in the dielectrophoretic trap.

6. The method of claim 1, wherein a first electrode constitutes at least a first portion of the elongated object, a second electrode constitutes at least a second portion of the elongated object, and wherein the first electrode is insulated from the second electrode.

7. The method of claim 1, comprising generating the electromagnetic field proximate to a plurality of tips, at least one of which is formed by the elongated object, so as to support a dielectrophoretic trap proximate to the plurality of tips.

8. The method of claim 1, further comprising trapping a particle in the dielectrophoretic trap.

9. The method of claim 8, wherein the particle is a cell.

10. The method of claim 8, further comprising moving the particle from a first location to a second location by moving the elongated object to at least one desired location.

11. A method, comprising:
   generating an electromagnetic field proximate to a plurality of tips, at least one of which is formed by an elongated object, so as to support a dielectrophoretic trap proximate to the plurality of tips; and moving the plurality of tips from a first location to a second location.

12. The method of claim 11, comprising generating an electromagnetic field proximate to at least four tips.

13. The method of claim 11, wherein a first electrode constitutes at least a first portion of the elongated object, a second electrode constitutes at least a second portion of the elongated object, and wherein the first electrode is insulated from the second electrode.

14. The method of claim 11, further comprising trapping a particle in the dielectrophoretic trap.

15. The method of claim 14, wherein the particle is a cell.

16. The method of claim 14, further comprising moving the particle from a first location to a second location by moving the elongated object from a first location to a second location.

* * * * *